United States Patent [19]
Kitazato et al.

[11] Patent Number: 5,993,797
[45] Date of Patent: Nov. 30, 1999

[54] VASCULAR INTIMAL HYPERPLASIA-INHIBITORY COMPOSITION

[75] Inventors: Kenji Kitazato, Tokushima; Yasundo Yamazaki, Iruma, both of Japan

[73] Assignee: Taiho Pharmaceutical Co., Ltd., Tokyo, Japan

[21] Appl. No.: 08/894,366

[22] PCT Filed: Dec. 16, 1996

[86] PCT No.: PCT/JP96/03662

§ 371 Date: Aug. 19, 1997

§ 102(e) Date: Aug. 19, 1997

[87] PCT Pub. No.: WO97/22628

PCT Pub. Date: Jun. 26, 1997

[30] Foreign Application Priority Data

Dec. 20, 1995 [JP] Japan ................................. 7-331758

[51] Int. Cl.⁶ .................... A61K 31/715; A61K 35/56; C08B 37/00
[52] U.S. Cl. ........................ 424/78.3; 424/520; 514/54; 514/824; 536/122; 536/123; 536/124

[58] Field of Search ..................... 424/488, 78.3, 424/520; 514/54, 824; 536/122, 123, 124, 127

[56] References Cited

U.S. PATENT DOCUMENTS 5,519,010  5/1996  Fan et al. .
5,646,130  7/1997  Shi .
5,770,205  6/1998  Collin .

FOREIGN PATENT DOCUMENTS 0 408 770  1/1991  European Pat. Off. .

*Primary Examiner*—Edward J. Webman
*Attorney, Agent, or Firm*—Nikido Marmelstein Murray & Oram, LLP

[57] ABSTRACT

The invention provides an excellent vascular intimal hyperplasia-inhibitory composition which comprises a sea cucumber-derived sulfated polysaccharide as an active ingredient and which causes no hemorrhagic symptoms and is useful particularly in the prevention of post-PTCA restenosis of the coronary arteries.

6 Claims, No Drawings

VASCULAR INTIMAL HYPERPLASIA-INHIBITORY COMPOSITION

TECHNICAL FIELD

The present invention relates to a novel composition for inhibiting vascular intimal hyperplasia.

BACKGROUND ART

Percutaneous transluminal coronary angioplasty (hereinafter referred to as "PTCA") is a therapeutic technique recently developed for nonsurgical treatment of coronary artery diseases. Thus, the technique comprises mechanically dilating the stenosed coronary artery by means of an inflatable balloon. However, PTCA cannot be a radical treatment of coronary artery diseases. It is known that in about 40% of the cases treated by PTCA for coronary stenosis, restenosis occurs several months after operation. Reportedly, this restenosis is mainly caused by cellulofibrous hyperplasia of the intima due to migration of smooth muscle cells from the media to the intima upon stimulation by various factors (platelet-derived growth factor, thrombin, etc.) resulting from platelet aggregation and blood clotting at the site of injury by PTCA and the subsequent proliferation of the smooth muscle cells in the intima [British Heart Journal, 58, 635–643 (1987); Human Pathology, 20, 477–485 (1989)].

To prevent this restenosis, various drugs including anticoagulants such as heparin, etc., platelet aggregation inhibitors such as aspirin, dipyridamole, ticlopidine, prostacyclin and its derivatives, etc., cell proliferation inhibitors such as ketanserin, and antilipidemics such as eicosapentaenoic acid, lovastatin, etc. have been tested preclinically or clinically but none of them proved to be sufficiently effective from the clinical viewpoint [inter alia, American Heart Journal, 117, 777–782 (1989); ibid., 119, 232 (1990); ibid., 122, 171–187 (1991); Circulation, 81, 1753–1761 (1990); Lancet, 177–181 (1989)].

With heparin, in particular, it has been reported that its long-term use (10,000 units/day, s.c.) following coronary angioplasty resulted in coronary restenosis in 82% of the cases, a very high figure as compared with control (restenosis value: 33%), with abnormal hemorrhage supervening in 41% [Journal of American College of Cardiology, 17 (2), 181A, (1991)]. This augmentation of bleeding tendency has been cited as one of the adverse effects of heparin, and heparin may cause not only hemorrhage at the administration site but also bleeding in the gastrointestinal tract and, in serious cases, even intracranial hemorrhage, with death from massive loss of blood ensuing in the worst cases.

Meanwhile, it is known that sulfated polysaccharides containing a heparin fragment which consists of 2 to 8 heparin- or haparan sulfate-derived saccharide units have a proliferation inhibitory action on smooth muscle cells (Japanese Kohyo Tokkyo Koho H04-503950 and H06-506973). Those heparin fragment-containing compounds, which are deprived of the antithrombin III-mediated antithrombin activity of heparin [Blood, 79, 1–17 (1992)], are expected to be attenuated in the bleeding-promoting effect based on the antithrombin activity of heparin. However, since the inhibition of abnormal smooth muscle proliferation by heparin in vivo is considered to involve, as one of the mechanisms thereof, said antithrombin III-mediated antithrombin activity, deprivation of this activity is considered to detract from the smooth muscle proliferation inhibitory effect.

Under the circumstances, development of a drug which would inhibit post-PTCA restenosis of the coronary arteries and hence intimal hyperplasia in atherosclerosis and be of clinical value has been awaited.

DISCLOSURE OF THE INVENTION

As mentioned above, the state of the art is that no effective vascular intimal hyperplasia-inhibitory agent, particularly no agent capable of preventing post-PTCA restenosis of the coronary arteries, has been discovered as yet. The primary object of the present invention, therefore, is to provide an excellent vascular intimal hyperplasia-inhibitory composition.

As a result of their intensive investigations, the present inventors found that a sea cucumber-derived sulfated polysaccharide has vascular intimal hyperplasia-inhibitory activity and is effective in preventing post-PTCA restenosis of the coronary arteries. The present invention has been completed based on such finding.

The present invention provides a vascular intimal hyperplasia-inhibitory composition which comprises an effective amount of a sea cucumber-derived sulfated polysaccharide and a pharmaceutically acceptable carrier therefor.

The present invention further provides a use for the sea cucumber-derived sulfated polysaccharide in preparing said vascular intimal hyperplasia-inhibitory composition comprising said sea cucumber-derived sulfated polysaccharide.

The present invention still further provides a method of inhibiting vascular intimal hyperplasia which comprises administering to a patient an effective amount of a sea cucumber-derived sulfated polysaccharide.

The vascular intimal hyperplasia-inhibitory composition of the present invention is a pharmaceutical composition comprising a sea cucumber-derived sulfated polysaccharide as an active ingredient. This sea cucumber-derived sulfated polysaccharide is a known compound described, for example in Japanese Kokai Tokkyo Koho S63-10601 and S63-128001 as well as Laid-open International Patent Specification WO 90/08784 and WO 90/09181. Said compound is known as a therapeutic agent for disseminated intravascular coagulation syndrome, as an anti-HIV agent and as an antithrombotic agent. It is quite unknown, however, that said sulfated polysaccharide would be useful as a vascular intimal hyperplasia-inhibitory agent.

The sea cucumber-derived sulfated polysaccharide to be used in accordance with the present invention inhibits abnormal post-PTCA proliferation of smooth muscles. The mechanisms of its action are similar to those of heparin but are considered to involve a heparin cofactor II-mediated antithrombin action, which differs from the case of heparin in decreased risks for hemorrhage. It is therefore an outstanding feature of said sulfated polysaccharide that it has very low bleeding-promoting activity as compared with heparins.

The sea cucumber-derived sulfated polysaccharide to be used in the practice of the present invention may be in the form in which the sulfate and carboxylic groups it contains are free or in the form in which said groups occur as pharmaceutically acceptable salts. Either form can be used as the active ingredient of the vascular intimal hyperplasia-inhibitory composition of the present invention. The sea cucumber-derived sulfated polysaccharide is clearly distinguished from other known sulfated polysaccharides and characterized especially by its high fucose content.

As such sulfated polysaccharide, there may be mentioned a sulfated polysaccharide extracted from the body wall of the invertebrate sea cucumber (holothurian) (such sulfated polysaccharide hereinafter referred to as "FGAG") and a sulfated polysaccharide derived from FGAG by depolymerization (hereinafter referred to as "DHG"), among others.

FGAG is a kind of chondroitin sulfate and has the following physicochemical characteristics:
(1) Description: A highly hygroscopic, white, amorphous powder.
(2) Molecular weight: About 15,000 to 80,000 (as determined by high-performance GPC or polyacrylamide gel electrophoresis).
(3) Composition analysis: As shown below.

| Galactosamine | 13 to 20% by weight |
|---|---|
| Glucuronic acid | 11 to 19% by weight |
| Fucose | 10 to 28% by weight |
| Sulfate group | 27 to 38.5% by weight |

The mole ratio being as shown below. Galactosamine-:glucuronic acid:fucose:sulfate=1:1±0.2:1.35±0.35:3.6±0.6.

The weight composition data shown in the present specification for the sulfated polysaccharide are, as a rule, values for the non-salt-forming form, namely the free form.

For the galactosamine, glucuronic acid, fucose and sulfate group assays, the following methods were employed.
(i) Galactosamine
    The White method (Carbohydrate Research, 114: 201, 1983).
(ii) Glucuronic acid
    The Bitter-Muir method (Analytical Biochemistry, 4: 330, 1962).
(iii) Fucose
    The Dische method (Journal of Biological Chemistry, 175: 595, 1948).
(iv) Sulfate group
    The Dodgson & Price method (Biochemical Journal, 84: 106, 1962).

FGAG is a known substance described, for example in Yao Hsueh Hsueh Pao, 15 (5), 263–270, 1980, Zhongyao Tongbao, 7 (4), 27–29, 1982, Yaoxue Xuebao, 18 (3), 203–208, 1983, and Japanese Kokai Tokkyo Koho S63-10601 and S63-128001 and can be expediently produced by the methods described therein.

More specifically, it is produced by degrading the body wall (paries) of the invertebrate sea cucumber (holothurian) with an alkali, further degrading it with an enzyme such as pancreatin, extracting, and isolating and purifying from the extract. Generally, the following sea cucumber species, among others, can be used in preparing FGAG:

*Stichopus japonicus* Selenka,
*Stichopus chloronoyus* Brandt,
*Stichopus variegatus* Semper,
*Holothuria pervicax* Selenka,
*Holothuria atra,*
*Holothuria argus,*
*Holothuria edulis,*
*Holothuria scabra,*
*Parastichopus nigripunctatus,*
*Thelenota ananas,*
*Holothuria monacaria* Lesson,
*Holothuria leucospilota* Brandt,
*Cucumaria chronhjelmi,*
*Cucumaria echinata,*
*Cucumaria frondosa* Japonica,
*Pentacta australis,*
*Paracaudina chilensis ransonneti,*
*Molpadia musculus,*
*Leptosynapta inhaerens,*
*Polycheira rufescens,*
*Synapta maculata,*
*Halodeima cinerascens* (Brandt),
*Actinopyga lacanora* (Jaeger),
*Actinopyga echinites* (Jaeger),
*Microthele nobilis* (Selenka), etc.

The sea cucumber to be used as the starting material may be a raw sea-cucumber or dried one. Of the sea cucumbers listed above, *Stichopus japonicus* Selenka is the most preferred starting material.

Among the sulfated polysaccharides derived from FGAG by depolymerization, the substance DHG obtained by depolymerization of FGAG is particularly preferred.

DHG can be readily produced by the method described in Laid-open International Patent Specification WO 90/08784 or WO 90/09181, for instance. Thus, it is produced by dissolving FGAG or a salt thereof in water and subjecting the same to depolymerization. The depolymerization reaction converts heparin or a like high-molecular-weight sulfated polysaccharide to a low-molecular-weight sulfated polysaccharide. Generally, reaction is carried out using a depolymerizing agent. Examples of the depolymerizing agent that can be used are hydrogen peroxide, hypohalous acids and salts thereof, such as hypochlorous acid, hypobromous acid and sodium hypochlorite, periodic acids and salts thereof, such as periodic acid and sodium periodate. A reaction accelerator such as ascorbic acid or the ferrous ion may further be used. The depolymerization reaction may also be induced by applying ultrasonic waves, radiations such as ultraviolet rays or gamma rays or the like either alone in lieu of the depolymerizing agent or in combination with the depolymerizing agent mentioned above. The most preferred depolymerization method uses hydrogen peroxide as the depolymerizing agent. The amount of hydrogen peroxide to be submitted to reaction is such that the hydrogen peroxide concentration will be 1 to 31% by weight, preferably 1 to 16% by weight. The reaction time is usually 1 to 60 hours, preferably 3 to 40 hours, and the reaction temperature is within the range of room temperature to 80° C., preferably about 40° to 60° C. The reaction with hydrogen peroxide is carried out at a pH from 1 to 8, preferably in an acidic to neutral range of pH 3 to 7. For maintaining the pH at a constant level, the reaction may be carried out in a buffer such as acetate buffer, phosphate buffer or Tris buffer, or a pH controller in which diluted sodium hydroxide or the like is employed may be used in carrying out the reaction. After completion of the reaction, the pH is returned to neutrality for isolation and purification. The isolation and purification can be carried out, for example, by fractional precipitation using an organic solvent such as ethanol or acetone, an acetate such as potassium acetate, barium acetate, calcium acetate or ammonium acetate, or a quaternary ammonium salt such as a cetyltrimethylammonium salt, by ion exchange chromatography using a resin such as DEAE-Cellulose (product of Sigma Chemical Co.), DEAE-Toyopearl (product of Tosoh Corporation), DEAE-Cellulofine (product of Chisso Corporation) or Dowex-1 (product of Dow Chemical Co.), by gel filtration chromatography using a resin such as Sephadex G-50 (product of Pharmacia-LKB Biotechnology) or Sephadex G-200 (product of Pharmacia-LKB Biotechnology), by dialysis using Spectra/Pore (product of Spectrum Medical Industries, Inc.) or the like or, further, by ultrafiltration. These means may be employed either alone or in an appropriate combination.

The thus-produced DHG has the following physicochemical characteristics:

(1) Description: A highly hygroscopic, amorphous, white powder.
(2) Molecular weight: 3,000 to 42,000.

The preferred molecular weight of DHG is about 4,000 to 15,000 (as determined by high-performance GPC).

(3) Composition analysis: DHG comprises galactosamine, glucuronic acid and fucose as constituent saccharides and contains sulfate groups, the composition being as follows:

| Weight composition | |
|---|---|
| Galactosamine | 18 to 24% by weight |
| Glucuronic acid | 14 to 21% by weight |
| Fucose | 13 to 20% by weight |
| Sulfate group | 31 to 44% by weight |

Mole ratio:
Galactosamine:glucuronic acid:fucose:sulfate= 1:0.80±0.20:0.85±0.15:3.4±0.90.

(4) Specific rotation: $[\alpha]^{20}_D = -55°$ to $-73°$ (c=1%).

Other physicochemical properties of DHG are as follows:

(5) Solubility: Soluble in water and insoluble in organic solvents such as ethanol and acetone.
(6) Color reactions: As shown below:

| | |
|---|---|
| Elson-Morgan reaction | + |
| Carbazole-sulfuric acid reaction | + |
| Cysteine-sulfuric acid reaction | + |
| Orcinol-hydrochloric acid reaction | + |
| Azure A metachromasia reaction | + |

As indicated by the above analytical results, FGAG and DHG have sulfate and carboxyl groups within their molecules and said groups can react with various bases to form salts. These sulfated polysaccharides are stable when they are in salt form. Thus, they are generally isolated in the form of a salt such as sodium and/or potassium salt. These sulfated polysaccharides in salt form can be converted to the corresponding free sulfated polysaccharides by treatment with a cation exchange resin such as Dowex 50W. These may further be converted to various desired salts by using conventional salt exchange techniques. Usable as the sulfated polysaccharide salts are pharmaceutically acceptable salts, for example salts with alkali metals such as potassium and sodium or alkaline earth metals such as calcium, magnesium and barium, or salts with organic bases, such as the pyridinium salt.

Among the active ingredients to be used in the practice of the present invention, those sulfated polysaccharides which have a high fucose content, preferably 10 to 28% by weight, are preferred. Such preferred sulfated polysaccharides contain galactosamine, glucuronic acid and sulfate groups as other constituents and have a molecular weight of about 3,000 to 100,000 (high-performance GPC or polyacrylamide electrophoresis).

Those sulfated polysaccharides which have the following physicochemical characteristics are preferably used in the practice of the present invention:

(1) Description: A highly hygroscopic, amorphous, white powder.
(2) Molecular weight: About 3,000 to 80,000 (high-performance GPC or polyacrylamide electrophoresis).

(3) Composition analysis:

| Weight composition | |
|---|---|
| Galactosamine | 13 to 24% by weight |
| Glucuronic acid | 11 to 21% by weight |
| Fucose | 10 to 28% by weight |
| Sulfate group | 27 to 44% by weight |

Mole ratio:
Galactosamine:glucuronic acid:fucose:sulfate= 1:0.80±0.40:1.20±0.50:3.40±0.90.

More preferred are those sulfated polysaccharides which are obtained by depolymerization and have the following physicochemical characteristics:

(1) Description: A highly hygroscopic, amorphous, white powder.
(2) Molecular weight: About 3,000 to 42,000 (high-performance GPC). A particularly preferred molecular weight is within the range of 4,000 to 15,000.
(3) Composition analysis:

| Weight composition | |
|---|---|
| Galactosamine | 18 to 24% by weight |
| Glucuronic acid | 14 to 21% by weight |
| Fucose | 13 to 20% by weight |
| Sulfate group | 31 to 44% by weight |

Mole ratio:
Galactosamine:glucuronic acid:fucose:sulfate= 1:0.80±0.20:0.85±0.15:3.40±0.90.

(4) Specific rotation: $[\alpha]^{20}_D = -55°$ to $-73°$ (c=1%).

These sulfated polysaccharides may be in free form or in the form of pharmaceutically acceptable salts, as mentioned hereinabove.

The vascular intimal hyperplasia-inhibitory composition of the present invention is prepared in the form of a pharmaceutical composition using an effective amount of a sea cucumber-derived sulfated polysaccharide and a phamaceutically acceptable carrier therefor in the conventional manner. The carrier to be used here includes various carriers commonly used in ordinary pharmaceutical compositions, for example excipients, binders, disintegrators, lubricants, colorants, flavorings, perfumes, surfactants, etc.

The unit dosage form of the vascular intimal hyperplasia-inhibitory composition of the present invention, particularly when it is used for the treatment and prevention of post-PTCA restenosis of the coronary arteries, is not limited to any particular one but can suitably be selected according to the therapeutic and prophylactic purposes, more specifically from among oral dosage forms such as tablets, coated tablets, pills, capsules, powders, granules, fine granules, solutions, emulsions and suspensions and parenteral dosage forms such as injections, suppositories, ointments, plasters, adhesives and the like. These dosage forms are prepared by conventional pharmaceutical methods generally known in this field of art.

The carrier to be used in producing tablet forms includes, among others, excipients such as lactose, sucrose, sodium chloride, glucose, urea, starch, calcium carbonate, kaolin, crystalline cellulose and silicic acid, binders such as water, ethanol, propanol, simple syrup, glucose solution, starch solution, gelatin solution, carboxymethylcellulose, shellac, methylcellulose, potassium phosphate and polyvinylpyrrolidone, disintegrators such as dry starch, sodium alginate, agar powder, laminaran powder, sodium hydrogen carbonate, calcium carbonate, polyoxyethylene-sorbitan fatty acid esters, sodium lauryl sulfate, stearic acid monoglyceride, starch and lactose, disintegration inhibitors such as sucrose, stearic acid, cacao butter and hydrogenated oils, absorption promoters such as quaternary ammonium bases and sodium lauryl sulfate, humectants such as glycerol and starch, adsorbents such as starch, lactose, kaolin, bentonite and colloidal silicic acid, and lubricants such as purified talc, stearic acid salts, boric acid powder and polyethylene glycol. When necessary, the tablets may further be provided with a conventional coating to give sugar-coated tablets, gelatin-encapsulated tablets, enteric tablets, film-coated tablets, double layer tablets, multilayer tablets and so on.

The carrier to be used in producing pill forms includes, among others, excipients such as glucose, lactose, starch, cacao butter, hydrogenated vegetable oils, kaolin and talc, binders such as gum arabic powder, tragacanth powder, gelatin and ethanol, and disintegrators such as laminaran and agar.

Capsules are generally produced by filling, in the conventional manner, hard gelatin capsules, soft capsules or the like with mixtures of the active ingredient with various carriers such as those specifically mentioned above.

The base to be used in producing suppositories includes, among others, polyethylene glycol, cacao butter, higher alcohols, higher alcohol esters, gelatin and semisynthetic glycerides.

The solutions, emulsions and suspensions, when prepared as injections, are sterilized, and are preferably isotonic with blood. The diluent to be used in preparing these forms includes, among others, water, aqueous solutions of lactic acid, ethyl alcohol, macrogol, propylene glycol, ethoxylated isostearyl alcohol, polyoxylated isostearyl alcohol and polyoxyethylenesorbitan fatty acid esters. In this case, sodium chloride, glucose or glycerol may be added to the pharmaceutical preparations in an amount sufficient to give isotonic solutions. Solubilizers, buffers, analgesics and other additives in common use may be added.

Ointments, for example pastes, creams and gel forms, are prepared by admixing the active ingredient compound with ointment bases in ordinary use, when necessary together with stabilizers, humectants, preservatives and so forth. As the bases, there may be mentioned liquid paraffin, white petrolatum, white beeswax, paraffin and the like. As the preservatives, there may be mentioned methyl p-hydroxybenzoate, ethyl p-hydroxybenzoate, propyl p-hydroxybenzoate and the like.

Transdermal drug delivery systems can be produced by applying the ointments, pastes, creams, gels or the like to ordinary supporting members. Suitable supporting members are woven or nonwoven fabrics made of cotton, staple fibers or chemical fibers, and films or foamed resin sheets made of plasticized polyvinyl chloride, polyethylene, polyurethane or the like.

The pharmaceutical preparations mentioned above each may further contain one or more of colorants, preservatives, perfumes, flavorings, sweeteners and like additives and other medicinals.

The content of the active ingredient in the pharmaceutical preparations of the present invention is not particularly limited but may suitably be selected within a broad range. It is generally recommendable, however, that said content be about 1 to 70% by weight.

The method of administration of said pharmaceutical preparations is not limited to any particular one but may suitably be selected according to the preparation form, the age, sex and other patient factors, the severity of disease and symptoms and other factors. The tablets, pills, powders, solutions, suspensions, emulsions, granules and capsules are administered by the oral route. The suppositories are administered rectally. The injections are administered intravenously either alone or in admixture with an ordinary nutrient solution containing glucose, amino acids, etc. Further, the injections alone are administered intraarterially, intramuscularly, intradermally, subcutaneously or intraperitoneally. The ointments are applied to the skin or oral mucosa, among others.

The amount of the active ingredient to be contained in each unit dosage form mentioned above may vary depending on the symptom of the patient to which it is to be applied or on the dosage form. Generally, however, it is desirable that in the case of oral preparations, each unit dosage form should contain about 1 to 1,000 mg, in the case of injections, about 0.1 to 500 mg and, in the case of suppositories, about 5 to 1,000 mg. The daily dose of the active ingredient in the above dosage forms may vary depending on the symptom, body weight, age and sex of the patient and other conditions, hence cannot be specified in an absolute manner. Generally, however, the daily dose for adult humans is within the range of about 0.1 to 5,000 mg, preferably about 1 to 1,000 mg, which is administered once daily or in two to four divided doses daily.

BEST MODES FOR CARRYING OUT THE INVENTION

The following production examples and embodiment examples are given for more detailed explanation of the present invention. They are, however, by no means limitative of the scope of the present invention. In the examples, "%" is on the weight basis unless otherwise specified.

PRODUCTION EXAMPLE 1

Production of *Stichopus japonicus*-derived sulfated polysaccharide

One kilogram of dried *Stichopus japonicus* was immersed in 10 liters of warm water and allowed to swell overnight. The muscular tissue was removed and the body wall was homogenized. Potassium hydroxide was added to a normality of 1.0. The resulting mixture was treated at a temperature of 60° C. for 100 minutes and then adjusted to pH 8.5 with 6 N hydrochloric acid. After addition of 50 g of pancreatin, the mixture was stirred at 50° C. for 3 hours.

After removal of impurities by centrifugation, 4.3 liters of ethanol was added to the mixture and the resulting mixture was allowed to stand at 4° C. The resulting precipitate was collected, washed in sequence with 80% ethanol, anhydrous ethanol and acetone and then dried in vacuo to give 50 g of a crude product. This crude product (50 g) was dissolved in 3.5 liters of water and the insoluble matter was removed by centrifugation. The supernatant obtained was treated for precipitation with 5% sodium chloride and 40% ethanol and the resulting precipitate was collected by centrifugation. This precipitate was dissolved in 2.5 liters of water and, after adjustment to pH 10.5, the solution was decolorized by adding dropwise a 30% aqueous solution of hydrogen peroxide and the subsequent warming on a water bath maintained at 50° C. (about 3 hours). After cooling, the insoluble matter was removed by centrifugation. Potassium acetate (about 490 g) was added to the supernatant and the resulting mixture was allowed to stand overnight in a refrigerator maintained at 4° C. On the next day, the resulting precipitate was dissolved in 2 liters of water, the solution was cooled to 0° C., the pH was adjusted to 2.8 and the insoluble matter was removed by refrigerated centrifugation. After neutralization of the supernatant, 196 g of potassium acetate was added, the mixture was allowed to stand at 4° C., and the resulting precipitate was collected by centrifugation. The precipitate was again dissolved in water, potassium acetate was added to a concentration of 0.5 M, and the resulting mixture was allowed to stand overnight at 4° C. The precipitate was collected by centrifugation, washed with 40% methanol and then dissolved in 1 liter of water, followed by precipitation treatment with 5% sodium chloride and 40% ethanol. The precipitate was collected by centrifugation, washed in sequence with 80% methanol, anhydrous ethanol and acetone and dried under reduced pressure to give 17 g of a sodium/potassium salt of FGAG. This showed the following physicochemical constants:
Molecular weight: 55,000 (high-performance GPC).
Composition analysis: The weight composition in the salt form was as follows:

| | |
|---|---|
| Galactosamine: | 20.0% |
| Glucuronic acid: | 18.6% |
| Fucose: | 17.2% |
| Sulfate group: | 36.6% |
| Sodium: | 6.2% |
| Potassium: | 7.4% |

Two grams of this sodium/potassium salt of FGAG was dissolved in 14.7 ml of water, 5.3 ml of 30% aqueous hydrogen peroxide was added and the mixture was maintained at 45° C. for 14 hours. After cooling, the pH was returned to about 7, the reaction mixture was subjected to precipitation treatment with 2% sodium chloride and 40% ethanol. Lyophilization and drying under reduced pressure gave 1.64 g of a sodium/potassium salt of DHG. Its physicochemical constants were as follows:
Molecular weight: 10,800 (high-performance GPC).
Composition analysis: The weight composition in the salt form was as follows:

| | |
|---|---|
| Galactosamine: | 18.1% |
| Glucuronic acid: | 16.7% |
| Fucose: | 14.8% |
| Sulfate group: | 37.1% |
| Sodium: | 5.0% |
| Potassium: | 6.5% |
| Mole ratio: | |

Galactosamine:glucuronic acid:fucose:sulfate= 1:0.85:0.89:3.80.
Specific rotation: $[\alpha]^{20}_D = -72.2°$ (c=1%).

Example 1
Injection preparation
The sodium/potassium salt of DHG as obtained in Production Example 1 was dissolved in distilled water for injection to give a 5% aqueous solution. This solution was distributed, in portions each corresponding to 60 mg of the sea cucumber-derived sulfated polysaccharide, into vials for lyophilization, and lyophilization was carried out. As a solvent, 10 ml of physiological saline was attached to each vial.

Example 2
Injection preparation
An injection preparation was prepared according to the following formulation:

| | |
|---|---|
| DHG sodium/potassium salt obtained in Production Example 1 | 40 mg |
| Physiological saline | q.s. |
| Per ampule | 10 ml |

Example 3
Tablet
Tablets were prepared according to the following formulation:

| | |
|---|---|
| DHG sodium/potassium salt obtained in Production Example 1 | 10 mg |
| Corn starch | 65 mg |
| Carboxymethylcellulose | 20 mg |
| Polyvinylpyrrolidone | 3 mg |
| Magnesium stearate | 2 mg |
| Per tablet | 100 mg |

Example 4
Suppository
A suppository was prepared according to the following formulation:

| | |
|---|---|
| DHG sodium/potassium salt obtained in Production Example 1 | 50 mg |
| Witepsol W-35 (product of Dynamit-Nobel AG) | 950 mg |
| Per container | 1,000 mg |

Pharmacological Test Example 1
Vascular smooth muscle hyperplasia-inhibitory action
The endothelium was denuded from a rat aorta by means of a balloon and the effect of a sulfated polysaccharide on the subsequent intimal hyperplasia was checked. The test compound used was the sodium/potassium salt of DHG as obtained in Production Example 1 (hereinafter referred to as "DHG-1"). Under anesthesia, rats were subjected to abdominal midline incision, a 3F balloon catheter was inserted into the thus-exposed right iliac artery until its tip reached the thoracic aorta region. The balloon was inflated to thereby cause vascular endothelial denudation (Lab. Invest., 53, 523, 1985). Three days before this procedure, subcutaneous injection of DHG-1 (10 mg/kg) was started and the subcutaneous injection was continued once daily until day 14 after said procedure. On day 14, the thoracic aorta was excised, fixed with formalin and stained with H.E. (hematoxylin and eosin). The degree of intimal hyperplasia was expressed in terms of percentage of the thickness of the intima portion showing maximum hyperplasia to the thickness of the smooth tunica media portion. Heparin (sodium salt with potency 185.6 U/mg) was used as a positive control at a dose of 3 mg/kg. The results are shown in Table 1.

Since administration of heparin at the same dose of 10 mg/kg as in the case of DHG-1 caused very severe hemorrhage (side effect) at the site of subcutaneous administration, the single subcutaneous dose of heparin was set at 3 mg/kg, which was the maximum dose at which the bleeding time was not prolonged.

TABLE 1

| Test drug | Number of cases | Hyperplasia (%) | Inhibition (%) |
| --- | --- | --- | --- |
| None (control) | 6 | 72 | 0 |
| DHG-1 | 5 | 33 | 54 |
| Heparin | 5 | 47 | 35 |

DHG-1 showed a potent hyperplasia-inhibitory effect without causing any hemorrhagic symptom. With heparin, however, even at said lower dose as compared with DHG-1, moderate inflammation due to hemorrhage was observed at the site of subcutaneous injection, and the effect was weaker than that of DHG-1 in spite of administration at the maximum administrable dose. It was thus revealed that DHG-1 can be administered without worrying about adverse effects such as bleeding and that its effect is satisfactory.

Post-PTCA restenosis of the coronary arteries is caused by intimal hyperplasia resulting from proliferation of smooth muscle cells following their migration from the media to the intima. Therefore, the effect of DHG in this model proves that, unlike heparin, DHG produces its post-PTCA restenosis-inhibitory effect without any risk of bleeding.

Pharmacological Test Example 2
Smooth muscle cell proliferation-inhibitory action The medial smooth muscle layer was excised from the rat thoracic aorta and incubated by the explant method (J. Cell. Physiol., 142, 342, 1990). This smooth muscle cell culture was adjusted to 2×103 cells/200 μl culture fluid. On the next day, DHG-1, dissolved in a small amount of the culture fluid was added to a final concentration of 0 to 1.0 μg/ml and, after 5 days of incubation, viable cells were counted by the MTT method (J. Immunol. Methods, 65, 55, 1983) and the inhibition rate (%) was calculated. The results are shown in Table 2.

TABLE 2

| DHG-1 (μg/ml) | Inhibition (%) |
| --- | --- |
| 0 | 0 |
| 0.1 | 64 |
| 1.0 | 59 |

DHG-1 significantly inhibited the proliferation of vascular smooth muscle cells at concentrations not lower than 0.1 μg/ml.

Pharmacological Test Example 3
Smooth muscle cell migration-inhibitory action

Following the procedure of the above Pharmacological Test Example 2, a rat smooth muscle cell culture of 1×10$^5$ cells/ml culture fluid was prepared, DHG-1 was added to a final concentration of 0 to 10 μg/ml and 250 μl of the mixture was placed in the upper chamber of a two-layer culture plate. A solution (600 μl) of platelet-derived growth factor (PDGF) showing chemotaxis at 1 ng/ml and DHG-1 (final concentration 0 to 10 μg/ml) was introduced into the lower chamber. The boundary between the upper and lower chambers was made of a filter having a number of small openings allowing passage of smooth muscle cells. After allowing cell migration from the upper to the lower chamber for 6 hours, the contents of the lower chamber alone were incubated for 24 hours and, after fixation and staining with DIFF-QUIK (product of Kokusai Shiyaku Co.), cells were counted and the inhibition rate (%) was calculated. The results are shown in Table 3.

TABLE 3

| DHG-1 (μg/ml) | Inhibition (%) |
| --- | --- |
| 0 | 0 |
| 0.1 | 1 |
| 1.0 | 20 |
| 10.0 | 60 |

At concentrations not lower than 1.0 μg/ml, DHG-1 inhibited the migration of vascular smooth muscle cells in a dose-dependent manner.

The results of Pharmacological Test Examples 2 and 3 showed that the post-PTCA restenosis-inhibitory action of the sea cucumber-derived sulfated polysaccharide is expressed through inhibition of migration or proliferation of medial smooth muscle cells.

INDUSTRIAL APPLICABILITY

The sea cucumber-derived sulfated polysaccharide, which is the active ingredient of the vascular intimal hyperplasia-inhibitory composition of the present invention, inhibits the migration or proliferation of vascular smooth muscle cells and shows a potent inhibitory action on vascular smooth muscle proliferation. Unlike heparin, it causes no hemorrhagic symptom and is useful, in particular, as an inhibitory agent for post-PTCA coronary restenosis.

We claim:

1. A method of inhibiting vascular intimal hyperplasia which comprises administering to a patient in need thereof a vascular intimal hyperplasia inhibiting effective amount of a sulfated polysaccharide from a sea cucumber, which sulfated polysaccharide is an FGAG polysaccharide or is obtained by depolymerization of the FGAG polysaccharide.

2. The method according to claim 1, wherein said sulfated polysaccharide is the FGAG polysaccharide.

3. The method according to claim 1, wherein said sulfated polysaccharide has the following physicochemical characteristics:

(1) description: a highly hygroscopic, amorphous, white power;

(2) molecular weight: 3,000 to 80,000 (as determined by high-performance GPC or polyacrylamide electrophoresis); and (3) composition analysis:

| weight composition | |
| --- | --- |
| galactosamine | 13 to 24% by weight, |
| glucuronic acid | 11 to 21% by weight, |
| fucose | 10 to 28% by weight and |
| sulfate group | 27 to 44% weight, | wherein the mole ratio being:
galactosamine:glucuronic acid:fucose:sulfate= 1:0.80±0.40:1.20±0.50:3.40±0.90.

4. The method according to claim 1, wherein said sulfated polysaccharide is the product of depolymerization of the FGAG polysaccharide extracted from the sea cucumber body wall.

5. The method according to claim 4, wherein said sulfated polysaccharide has the following physicochemical characteristics:

(1) description: a highly hygroscopic, amorphous, white power;

(2) molecular weight: 3,000 to 42,000 (as determined by high-performance GPC);

(3) composition analysis:

| weight composition | |
|---|---|
| galactosamine | 18 to 24% by weight, |
| glucuronic acid | 14 to 21% by weight, |
| fucose | 13 to 20% by weight and |
| sulfate group | 31 to 44% weight, | wherein the mole ratio being:

galactosamine:glucuronic acid:fucose:sulfate= 1:0.80±0.20:0.85±0.15:3.40±0.90; and (4) specific rotation: $[\alpha]^{20}_D = -55°$ to $-73°$ (c=1%).

6. The method according to claim 5, wherein said sulfated polysaccharide has a molecular weight of 4,000 to 15,000 (as determined by high-performance GPC).

* * * * *